United States Patent [19]

Arnesen

[11] Patent Number: Plant 5,389

[45] Date of Patent: Jan. 15, 1985

[54] AZALEA NAMED NANCY MARIE

[75] Inventor: Richard A. Arnesen, Sylmar, Calif.

[73] Assignee: Geo. J. Ball Inc., West Chicago, Ill.

[21] Appl. No.: 504,961

[22] Filed: Jun. 16, 1983

[51] Int. Cl.[3] ..... A01H 5/00

[52] U.S. Cl. ..... Plt./55

[58] Field of Search ..... Plt./55

*Primary Examiner*—Robert E. Bagwill

*Attorney, Agent, or Firm*—Chas. W. Rummler

[57] ABSTRACT

A new and distinctive variety of azalea plant particularly adapted for greenhouse forcing and distinguished by its basically white flowers variegated by a middle stripe of a coral color about one-third the petal width and extending the length of the petal, the petal colors being very definitely segregated and producing a star-shaped display of color against an all white background. This plant has a vigorous, sturdy and well branched growth habit, with abundant foliage, a profuse production of blooms and capability of being bloomed at any time of the spring season.

1 Drawing Figure

BACKGROUND OF THE INVENTION

This new plant originated as a sport of the azalea variety "Variegated Dogwood", U.S. Plant Pat. No. 4,455, and was discovered by me in February 1982 at Sylmar, Calif., among greenhouse grown plants of the parent variety. The very attractive and distinctive appearance of the sport prompted me to reproduce it by original cuttings to observe its reproduction capability and because of material success in that regard, I continued propagation through successive generations and determined that the novel and distinctive characteristics of this new plant held true from generation to generation and appeared to be firmly fixed.

DESCRIPTION OF THE DRAWINGS

My new variety of azalea plant is illustrated by the accompanying photographic drawing, in which the upper view shows a single blossom in close-up detail and the lower view shows clusters of the flowers and foliage as they would appear looking down on a potted plant, the colors shown being as close to those specified as it is reasonably possible to obtain by conventional photographic procedures.

DESCRIPTION OF THE NEW AZALEA VARIETY

The following is a detailed description of my new variety of azalea plant as observed in greenhouse grown plants at West Chicago, Ill., in March of 1983, the color designations being according to The Horticultural Colour Chart (H.C.C.) of The British Colour Council as published by The Royal Horticultural Society of London, England.

THE PLANT

Origin: Sport.

Parentage: "Variegated Dogwood", U.S. Plant Pat. No. 4,455.

Classification:

*Botanic.*—Rhododendron.

*Commercial.*—Hybrid Azalea.

Form: Spreading bush for pot culture.

Height: Medium.

Growth: Vigorous, sturdy and well branched.

Foliage:

*Quantity.*—Abundant.

*Leaf shape.*—Oblanceolate to spatulate with a mucronate apex consisting of a tiny white point.

*Texture.*—Puberulous.

*Aspect.*—Glossy.

*Color.*—Upper side: Younger Leaves — Scheeles Green 860/2-860. Older Leaves — Ivy Green 0001060/2. Under side: Younger Leaves — Spinach Green 0960/3. Older Leaves — Spinach Green 0960/3.

*Venation.*—Alternate pinnate with the younger leaves having veins of 0960/3 and other leaves having veins of 0960.

THE BUD

Size: Medium.

*Length.*—About $\frac{3}{4}$ to $1\frac{1}{4}$ inches long.

*Diameter.*—About 5/16 to 7/16 inch.

Form: Oblanceolate and pointed.

Opening Rate: Bud opens quickly.

Color:

*When sepals first divide.*—White Variegated with Rose Opal 022/2.

*When petals begin to unfurl.*—White Variegated with Rose Opal 022/2.

Sepals: When flowers open, the sepals stand up.

Color:

*Inside.*—Pod Green 061.

*Outside.*—Pod Green 061/1.

Calyx:

*Size.*—Small.

*Shape.*—Funnel-shaped and deeply cleft.

*Splitting.*—Calyx splits.

*Aspect.*—Hairy.

Peduncle or flower stem:

*Length.*—About $\frac{1}{4}$ inch.

*Character.*—Erect.

*Color.*—Pod Green 061/1 (sometimes with a streak of Rose Opal 022 on upper side of peduncle).

THE FLOWER

Blooming habit: This plant blooms profusely once, at any time during the spring season.

Size of flower: Medium.

*Diameter.*—About 2 to 2½ inches.

*Depth.*—About 1¼ inch.

Borne: In clusters of two or three flowers occasionally with four flowers per cluster.

Flower shape:

*When bloom first opens.*—Funnel shaped.

*When bloom matures.*—The shape is substantially the same.

Petalage:

*Number of petals:*—Five.

*Arrangement.*—Slightly imbricated.

*Form.*—Generally, broadly ovate.

*Texture.*—Extraordinarily thick.

*Appearance.*—Satiny.

*Color.*—Outer petals: Body — White with middle stripe of Camellia Rose 622 to 622/1. Base — 622/2. Upper three petals are speckled with Tyrian Purple 727 near the base of petal. Reverse side — White with midstripe of Carmine 21/2. Inside petals: Body — White with middle stripe of Camellia Rose 622.

Petaloids: None.

Peduncle:

*Length.*—About ¼ to ⅜ inch.

*Character.*—Sturdy, erect and hairy.

*Color.*—Pod Green 061/1 with a streak of Rose Opal 022 on the upper side of the peduncle.

Discoloration after full bloom: Color fades with a bluish tinge as the flower dries.

Effect of hot weather: In hot weather, the color tends to fade and becomes somewhat lighter.

Disease resistance: This plant is resistant to water mold and cylindrocladium as observed in California where azaleas are predominantly grown.

Fragrance: None.

Lasting quality: On plant — Excellent. (Not recommended as a cut flower.)

REPRODUCTIVE ORGANS

Stamens:

*Anthers.*—Number — 5; occasionally 6 to 8. Arrangement: Regular encircling the pistil. Size: About ⅛ inch.

*Filaments.*—Length 13 1 to 1-3/16 inches. Color: Neyron Rose 623/3.

*Pollen.*—Color — White.

Pistils:

*Number.*—One.

*Stigma.*—Color — Camellia Rose 622.

Characteristics of ovaries: Superior.

This plant is particularly distinguished by its flower, which is star-shaped in color with each petal being consistently one-third coral surrounded by about one-third white on each side. Unlike its parent "Variegated Dogwood", the petal colors of the flowers of this plant are definitely segregated. Otherwise the general characteristics of this plant are like those of its parent.

I claim:

1. The new and distinct variety of azalea plant, substantially as herein shown and described, characterized by its basically white flower petals each having a longitudinal midsection of pink coloration which presents a star-like appearance for the fully opened flower.

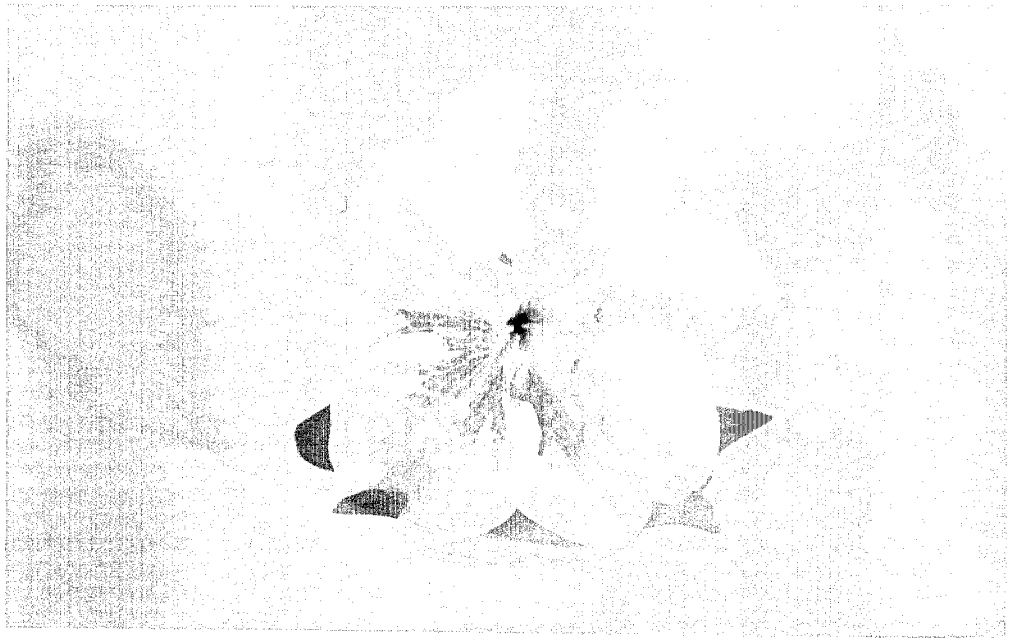
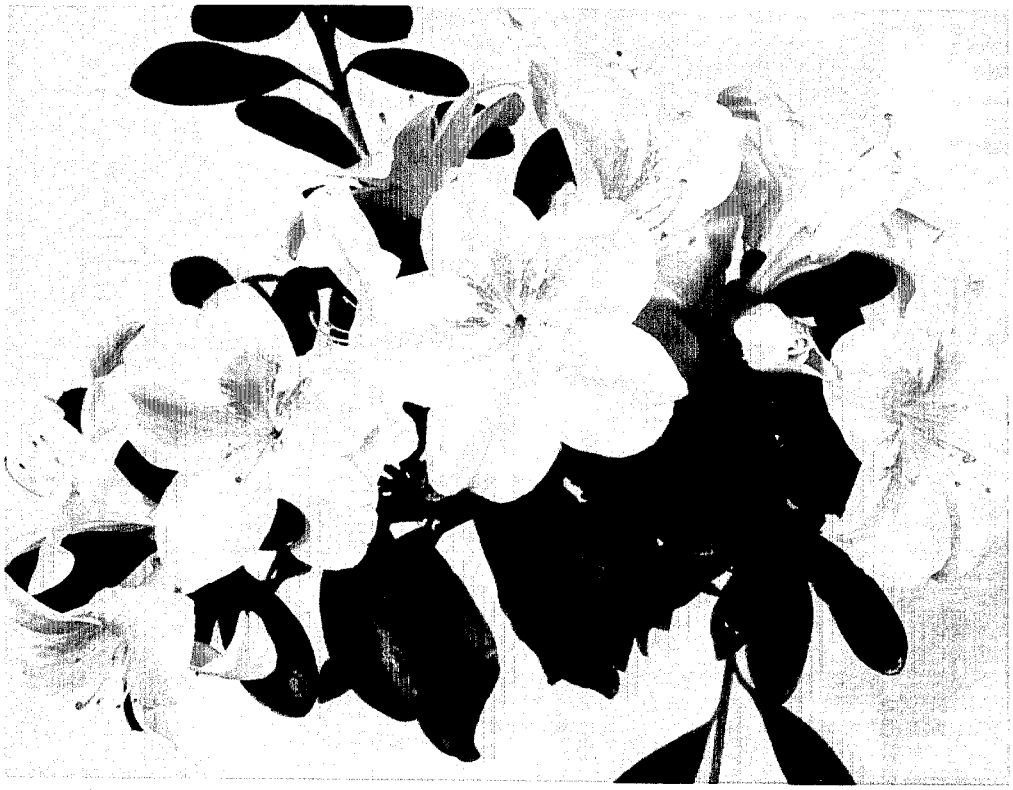

* * * * *